(12) United States Patent
Rensen et al.

(10) Patent No.: US 9,915,523 B2
(45) Date of Patent: Mar. 13, 2018

(54) SYSTEM FOR MONITORING THE POSITION OF A TUBE'S DISTAL END RELATIVE TO A BLOOD VESSEL

(75) Inventors: Judith Margreet Rensen, Eindhoven (NL); Wouter Harry Jacinth Rensen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 709 days.

(21) Appl. No.: 13/703,818

(22) PCT Filed: Jun. 10, 2011

(86) PCT No.: PCT/IB2011/052539
§ 371 (c)(1),
(2), (4) Date: Dec. 12, 2012

(87) PCT Pub. No.: WO2011/158159
PCT Pub. Date: Dec. 22, 2011

(65) Prior Publication Data
US 2013/0083331 A1    Apr. 4, 2013

(30) Foreign Application Priority Data
Jun. 17, 2010    (EP) .................................... 10166303

(51) Int. Cl.
*A61M 5/168*    (2006.01)
*G01B 11/14*    (2006.01)
(Continued)

(52) U.S. Cl.
CPC .............. *G01B 11/14* (2013.01); *A61B 5/065* (2013.01); *A61B 5/15003* (2013.01);
(Continued)

(58) Field of Classification Search
CPC ................ A61B 5/065; A61B 5/15003; A61B 5/150396; A61B 5/150511;
(Continued)

(56) References Cited

U.S. PATENT DOCUMENTS 3,563,090 A    2/1971    Deltour
4,191,184 A    3/1980    Carlisle
(Continued)

FOREIGN PATENT DOCUMENTS

JP    5317422 A    12/1993
JP    2004187936 A    7/2004
(Continued)

*Primary Examiner* — Ruth S Smith (57) ABSTRACT

The invention relates to a system for monitoring a position of a distal end of a tube with respect to a blood vessel of a mammal. The system comprises a source for generating an outgoing beam of electromagnetic radiation having a predefined electromagnetic spectrum. The system furthermore comprises a guideway for guiding the outgoing beam to the distal end, and for guiding an incoming beam of electromagnetic radiation reflected by surroundings of the distal end in response to said outgoing beam to a measurement arrangement, which is arranged for measuring a parameter associated with an electromagnetic spectrum of the incoming beam. The system furthermore comprises a comparator arrangement for comparing said parameter with a reference parameter associated with a reference electromagnetic spectrum representing a predefined location of the distal end inside the mammal.

35 Claims, 6 Drawing Sheets (51) Int. Cl.
　　　*A61B 5/15*　　　(2006.01)
　　　*A61B 5/153*　　(2006.01)
　　　*A61B 5/06*　　　(2006.01)
(52) U.S. Cl.
　　　CPC ........ *A61B 5/153* (2013.01); *A61B 5/150396* (2013.01); *A61B 5/150511* (2013.01); *A61B 5/150748* (2013.01); *A61M 5/16836* (2013.01); *A61M 2205/3306* (2013.01); *A61M 2205/3313* (2013.01)
(58) Field of Classification Search
　　　CPC ............. A61B 5/150748; A61B 5/153; A61M 2205/3306; A61M 2205/3313; A61M 5/16836; G01B 311/14
　　　See application file for complete search history.

(56)　　　　　References Cited

U.S. PATENT DOCUMENTS

| | | | |
|---|---|---|---|
| 4,877,034 A * | 10/1989 | Atkins et al. | ................. 600/475 |
| 4,971,068 A | 11/1990 | Sahi | |
| 4,981,138 A * | 1/1991 | Deckelbaum | ........ A61B 5/0071 600/477 |
| 5,346,466 A | 9/1994 | Yerlikaya | |
| 5,411,052 A | 5/1995 | Murray | |
| 5,899,665 A | 5/1999 | Makino | |
| 6,208,887 B1 * | 3/2001 | Clarke | ................. A61B 5/0075 356/301 |
| 6,736,801 B1 | 5/2004 | Gallagher | |
| 6,824,528 B1 | 11/2004 | Faries | |
| 2003/0216663 A1 | 11/2003 | Jersey-Willuhn | |
| 2004/0204651 A1 * | 10/2004 | Freeman | ............... A61B 5/0075 600/473 |
| 2008/0027313 A1 | 1/2008 | Shachar | |
| 2009/0118670 A1 | 5/2009 | Neerken et al. | |
| 2009/0137952 A1 | 5/2009 | Ramamurthy | |

FOREIGN PATENT DOCUMENTS

| | | |
|---|---|---|
| JP | 2006006919 A | 1/2006 |
| JP | 2008000218 A | 1/2008 |
| WO | WO 9915074 A1 * | 4/1999 |

* cited by examiner

SYSTEM FOR MONITORING THE POSITION OF A TUBE'S DISTAL END RELATIVE TO A BLOOD VESSEL

FIELD OF THE INVENTION

The invention relates to a system for monitoring a position of a distal end of a tube with respect to a blood vessel.

BACKGROUND OF THE INVENTION

U.S. Pat. No. 4,971,068 discloses a needle comprising a metal cannula and a temperature sensitive indicator mounted on the cannula. Blood vessel penetration is visually indicated by a change of color of the temperature sensitive indicator in case blood enters the cannula and reaches said temperature sensitive indicator.

A problem of the needle disclosed in U.S. Pat. No. 4,971,068 is that it is not capable of monitoring whether or not the cannula maintains a positioning inside the blood vessel during infusion procedures, i.e. procedures in which a liquid is supplied to the patient. Namely, the needle disclosed in U.S. Pat. No. 4,971,068 requires blood itself to flow into the cannula up to the temperature sensitive indicator in order to observe blood vessel penetration hence to observe the positioning of the cannula in the blood vessel. Hence, the needle disclosed in U.S. Pat. No. 4,971,068 only allows for application in sample taking procedures.

SUMMARY OF THE INVENTION

It is an object of the invention to provide a system of the kind defined in the opening paragraph, capable of monitoring whether or not a position inside a blood vessel is maintained for a distal end of a tube, both during sample taking and infusion procedures.

The object of the invention is achieved by the system according to the invention for monitoring a position of a tube's distal end relative to a blood vessel of a mammal. The system according to the invention comprises a source for generating an outgoing beam of electromagnetic radiation having a predefined electromagnetic spectrum, a guideway for guiding the outgoing beam to the distal end, and for guiding an incoming beam of electromagnetic radiation reflected by surroundings of the distal end in response to said outgoing beam to a measurement arrangement, the measurement arrangement for measuring a parameter associated with an electromagnetic spectrum of the incoming beam, and a comparator arrangement configured for comparing said parameter with a reference parameter associated with a reference electromagnetic spectrum representing a predefined location of the distal end inside the mammal.

Blood, and more particularly red blood cells, comprise hemoglobin, whereas the tissue surrounding a blood vessel does not or at least to a significantly smaller extent. Hemoglobin is a metalloprotein, containing iron, and serves the purpose of oxygen transport. Hemoglobin provides blood with distinct reflective and absorptive properties compared to tissue. Therefore, parameters associated with the electromagnetic spectrum of the incoming beam of electromagnetic radiation attainable in response to the outgoing beam of electromagnetic radiation are variant under reflectance by blood. For example red light, i.e. electromagnetic radiation having a wavelength in the range of 630 nm to 740 nm, is reflected relatively strongly whereas green light, i.e. electromagnetic radiation having a wavelength in the range of 490 nm to 560 nm, is reflected to a significantly smaller share i.e. absorbed relatively strongly. Hence, aforementioned parameters significantly differ if the tube's distal end of the tube is positioned inside the blood vessel compared to the situation in which it is positioned outside the blood vessel.

By measuring a particular parameter associated with the incoming beam's electromagnetic spectrum, and by comparing said parameter with a corresponding parameter of a reference electromagnetic spectrum attainable in response to the outgoing beam if the tube's distal end were positioned at a predefined location inside the patient, it is made ascertainable whether or not the distal end's position is at said location.

If the reference spectrum reflects the situation in which the predefined location is in the blood vessel, conformance between the latter qualities is indicative for a proper position of the tube's distal end, whereas a significant difference between the latter qualities indicates an incorrect position. If the reference spectrum depicts the situation in which the predefined location is outside the blood vessel, e.g. inside the tissue, the converse reasoning holds.

The incoming beam of electromagnetic radiation is reflected by the surroundings of the tube's distal end of the tube in response to the outgoing beam. Therefore, no blood is required to flow through the tube itself for the purpose of monitoring the distal end's position. As a result, the system according to the invention is capable of monitoring the distal end's position relative to the blood vessel during sample taking procedures in which blood is drawn from a patient through the tube, as well as infusion procedures in which a liquid flows towards the blood vessel via said tube.

Both during sample taking and infusion procedures, the position of the tube's distal end is prone to disturbances due to e.g. a patient's movements. If the distal end's position inside the blood vessel perishes, i.e. the distal end is no longer situated inside the blood vessel, the liquid is supplied to tissue surrounding said blood vessel. As a result of that, irritation, swelling and/or pain are caused for the patient. The system according to the invention is useful for detecting the latter situation, thereby enabling medical professionals to take appropriate measures.

It is furthermore to be noted that the system according to the invention is suitable for monitoring the tube's distal end positioning during all stages of the aforementioned procedures. That is, the system according to the invention allows for successful application not only during a process of exchanging liquids with the patient, yet also at the beginning of such a procedure which beginning is dedicated to blood vessel penetration.

In this document, a blood vessel is considered to include both veins and arteries.

It is to be noted that the spectrum of the outgoing beam is not limited to the visible share of the electromagnetic spectrum. That is, the spectrum may comprise wavelengths smaller than 380 nm as well as wavelengths exceeding 750 nm.

In this text, tube implies a duct for exchanging a liquid with a mammal patient, e.g. needles, cannulas, needles, soft catheters and the like.

In a preferred embodiment of the system according to the invention, the reference electromagnetic spectrum represents the situation in which the predefined location is in the blood vessel. This embodiment enables detecting a misalignment of the tube's distal end with respect to the blood vessel, even if that distal end is not positioned in the tissue surrounding the blood vessel, which is contrary to the embodiment in which the reference electromagnetic spectrum reflects the situation in which the predefined location is in the tissue surrounding the blood vessel. This embodiment therefore has the advantage that it is capable of more reliably monitoring the position of a distal end of a tube with respect to a blood vessel.

In a further preferred embodiment of the system according to the invention, the parameter associated with the electromagnetic spectrum is time dependency. In this embodiment, the parameter associated with the electromagnetic spectrum is not only variant under reflectance by blood; it is furthermore variant under blood flow rate. That is the red blood cells which are either uniformly or non-uniformly dispersed in the blood will reflect the incoming beam with a Doppler shift corresponding to their velocities. Said Doppler shift accordingly affects the time dependent behavior of the electromagnetic spectrum of the incoming beam. If the tube's distal end ceases to be positioned inside the blood vessel, the latter Doppler shift is no longer present. Therefore this embodiment advantageously enables detecting that the tube's distal end is not positioned in the blood vessel but remains surrounded by blood nonetheless. The latter situation may for instance occur when treating patients suffering from problematic coagulation of blood. For such patients, if the distal end ceases to be positioned inside the blood vessel and ends in the tissue surrounding the blood vessel, it will be surrounded by blood nonetheless.

In a practical embodiment of the system according to the invention, the parameter associated with the electromagnetic spectrum is spectral contents.

In a further practical embodiment of the system according to the invention, the parameter associated with the electromagnetic spectrum is spectral contents at a specific wavelength. This embodiment is advantageous in that it facilitates the operation for the system while allowing for a clear and unambiguous detection of a possible misalignment of the tube's distal end with respect to the blood vessel. For instance, the absorption spectrum of blood is particularly strong for wavelengths of about 400 nm, contrary to the absorption spectrum of the tissue surrounding the blood vessel. The latter distinctive absorption characteristic is accordingly reflected by the electromagnetic spectrum of the incoming beam and therefore constitutes a basis for determining whether or not the distal end is positioned inside the blood vessel.

In a further preferred embodiment of the system according to the invention, the specific wavelength is in the range of 630 nm to 730 nm. Blood reflects wavelengths in the range of 630 nm to 730 nm relatively strong compared to the wall of the blood vessel. Therefore this embodiment is advantageous in that it allows for accurately registering whether the distal end occupies a position in the blood vessel or a position exterior to the blood vessel but near to its wall.

In a further practical embodiment of the system according to the invention, a wall of the tube is configured for performing as the guideway. This embodiment enables integration of multiple functionalities, i.e. transporting a liquid either towards the patient or from the patient, guiding the outgoing beam towards the patient and transferring the incoming beam towards the measurement arrangement, into a single component thereby reducing the number of components comprised in the system. As a result, this embodiment advantageously increases the economic feasibility of disposing the tube after a single use.

In a further preferred embodiment of the system according to the invention, the guideway is arranged for receiving a liquid for the purpose of guiding the outgoing beam and the incoming beam. In this embodiment, the performance of the guideway is dependent on the amount of liquid present in the tube. If no liquid is present, neither the outgoing nor the incoming beams are transferred. Therefore, in addition to effectively reducing the costs associated with realizing the guideway, this embodiment advantageously enables detecting whether the liquid supply towards the patient or the sample taking from the patient is interrupted. Such interruptions may be caused by the liquid container attached to the tube running empty and by obstructions in the tube due to sharp bents.

In a further preferred embodiment of the system according to the invention, the tube comprises an optical fiber for performing as the guideway. This embodiment has the advantage of providing a guideway having excellent optical properties, e.g. total internal reflection is guaranteed, without negatively affecting the handling properties of the system for the medical professional, and without negatively impacting patient convenience.

A further preferred embodiment of the system according to the invention comprises a drip chamber for temporarily storing a liquid dripping from a liquid container during use, wherein the drip chamber comprises an optical element configured for assisting the guideway in guiding the outgoing beam of electromagnetic radiation from the source to the distal end, which optical element has a transparent part in response to coverage by the liquid in the drip chamber and a reflective part in response to non-coverage by the liquid in the drip chamber. Hence, the optical element allows the outgoing beam to pass when submerged in the liquid whereas it impedes the outgoing beam from passing when surrounded completely by air. As a result, the incoming beam is dependent on the amount of liquid present in the drip chamber. Therefore, this embodiment is advantageously capable of detecting whether the liquid in the drip chamber level has fallen below some critical level.

A further preferred embodiment of the system according to the invention comprises a drip chamber for temporarily storing a liquid dripping from a liquid container during use, wherein the source is configured for providing the outgoing beam of electromagnetic radiation with an orientation intersecting an imaginary axis along which the liquid during operational conditions drops from the liquid container towards the tube. Here, intersection implies that the outgoing beam is not parallel to the imaginary axis. Each time a liquid drop crosses the outgoing beam of electromagnetic radiation, said beam will be reflected. Therefore the frequency at which the outgoing beam is thus reflected this way conforms to the liquid drop rate. Presuming the average liquid drop size is known, the frequency at which the outgoing beam is reflected constitutes a measure for the rate at which the liquid is being supplied towards the patient. As a result this embodiment has the advantage that it provides for registering the liquid supply rate.

A further preferred embodiment of the system according to the invention comprises a drip chamber for temporarily storing a liquid dripping from a liquid container during use, wherein the source is configured for providing the outgoing beam of electromagnetic radiation with an orientation intersecting an interface of the liquid in the drip chamber. Each time a liquid drop touches the interface i.e. the surface of the liquid in the drip chamber, a surface wave is induced which alters the reflection of the outgoing beam by the interface of the liquid. Therefore the frequency at which the reflection of the outgoing beam is altered this way must conform to the liquid drop rate. Presuming the average liquid drop size is known, the frequency at which the outgoing beam is reflected constitutes a measure for the liquid supply rate towards the patient. Therefore this embodiment advantageously enables registering the supply rate to the patient.

DETAILED DESCRIPTION OF THE EMBODIMENTS

Figure 1:
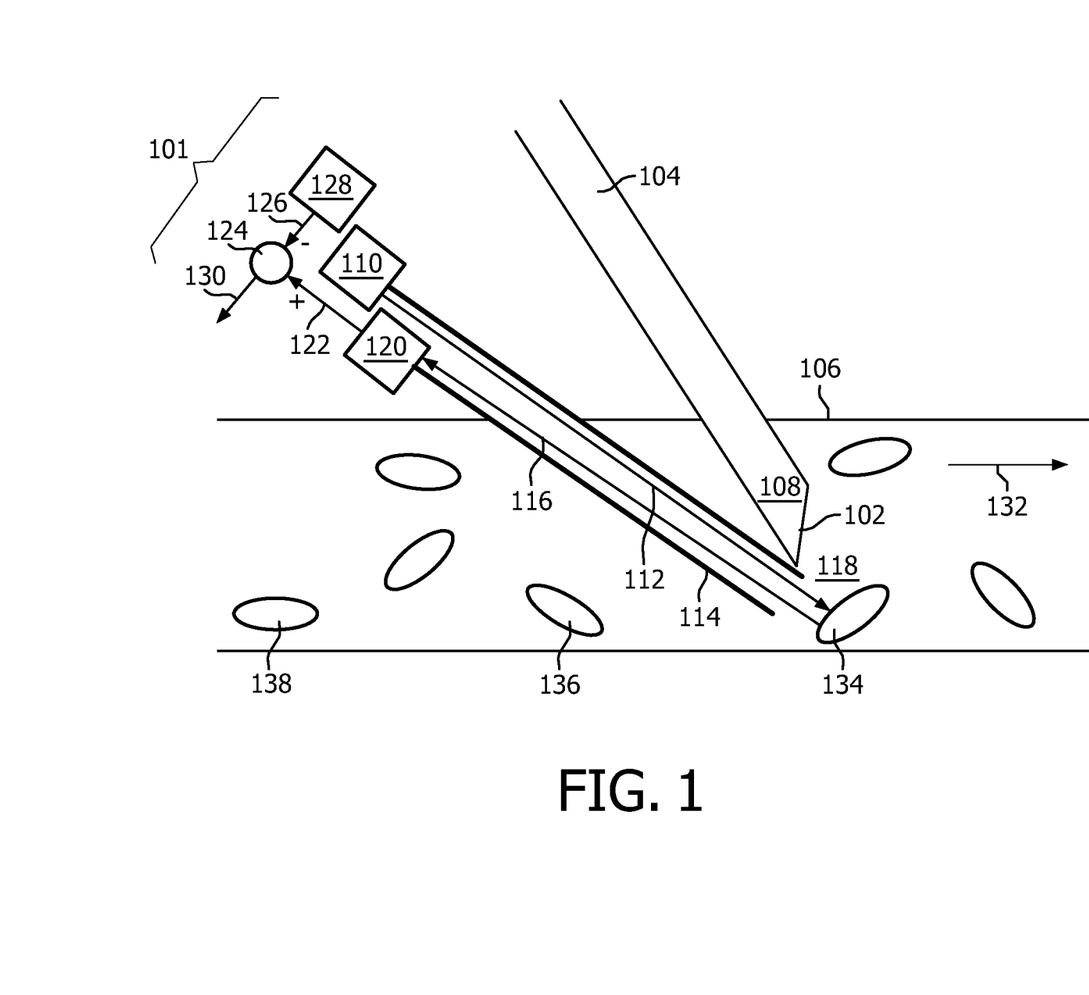
FIG. 1 schematically displays an embodiment of the system according to the invention in which the guideway is disconnected from the tube.

FIG. 1 schematically displays a system 101 for monitoring a position of a distal end 102 of a tube 104 with respect to a blood vessel 106. In this particular embodiment, the system 101 is employed for intravenous supply of a liquid 108 via the tube 104. Nonetheless, the system 101 may equally well perform for the purpose of taking samples from the blood vessel 106. The system 101 comprises a source 110 for generating an outgoing beam 112 of electromagnetic radiation having a predefined electromagnetic spectrum. The system 101 furthermore comprises a guideway 114 for transferring the outgoing beam 112 towards the distal end 102 of the tube 104. From FIG. 1 it becomes clear that the guideway 114 and the tube 104 need not necessarily be integrated into a single component. The guideway 114 is furthermore configured for transferring an incoming beam 116 of electromagnetic radiation reflected by surroundings 118 of the distal end 102 in response to said outgoing beam 112 of electromagnetic radiation to a measurement arrangement 120. The measurement arrangement 120 is arranged for measuring a parameter 122 associated with an electromagnetic spectrum of the incoming beam 116 of electromagnetic radiation. The latter parameter is variant under reflectance by blood, i.e. the parameter will differ if the surroundings 118 of the distal end 102 comprise blood compared to the situation in which the surroundings 118 do not comprise blood, e.g. if the surroundings 118 is the tissue surrounding the blood vessel 106. The system 101 furthermore comprises a comparator arrangement 124 configured for comparing the parameter 122 with a reference parameter 126 associated with a reference electromagnetic spectrum. The reference electromagnetic spectrum is attainable from the incoming beam 116 in response to the outgoing beam 112 if the distal end 102 were positioned at some predefined location inside the mammal patient. The reference parameter 126 may be stored in a memory 128. An output 130 of the comparator arrangement 124 enables a medical professional to draw conclusions regarding the position of the distal end 102 with respect to the blood vessel 106 and to accordingly provide for appropriate measures if the distal end 102 proves not to be positioned in the blood vessel 106, either because it has not entered the blood vessel 106 at the start of the infusion or sample-taking procedure or because it has ceased to be located in the blood vessel 106 for instance due to patient movement.

In a particular embodiment of the system 101, the reference electromagnetic spectrum reflects the situation in which the predefined location is inside the blood vessel 106. Hence, for this embodiment of the system 101 it holds that if the parameter 122 substantially equals the reference parameter 126, the distal end 102 is positioned in the blood vessel 106.

In a specific embodiment of the system 101, the measurement arrangement 120 is furthermore configured for measuring time dependency of the electromagnetic spectrum of the incoming beam 116. Given a particular blood flow rate and direction, as indicated by arrow 132, red blood cells 134, 136 and 138 consecutively reflect the outgoing beam 116 causing a Doppler shift according to the blood flow rate. For this purpose, the measurement arrangement 120 may be provided with a laser Doppler vibrometer known per se.

Figure 2A:
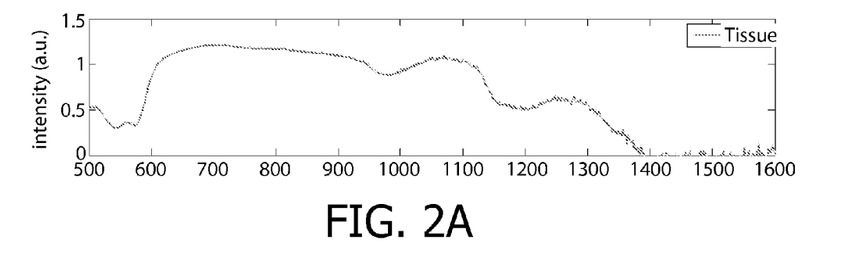
FIGS. 2A, 2B and 2C depict reflectance spectra for tissue, a blood vessel wall and blood, respectively.
Figure 2B:
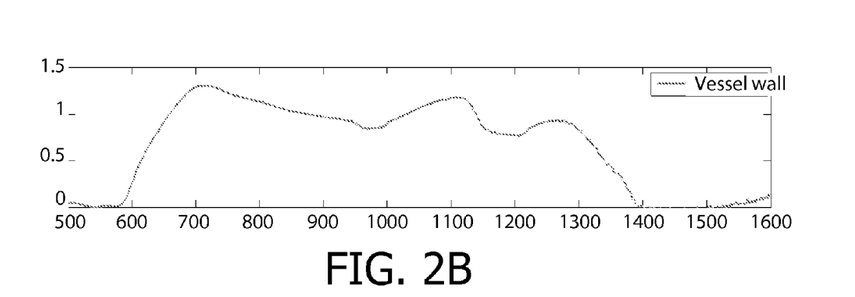
Figure 2C:
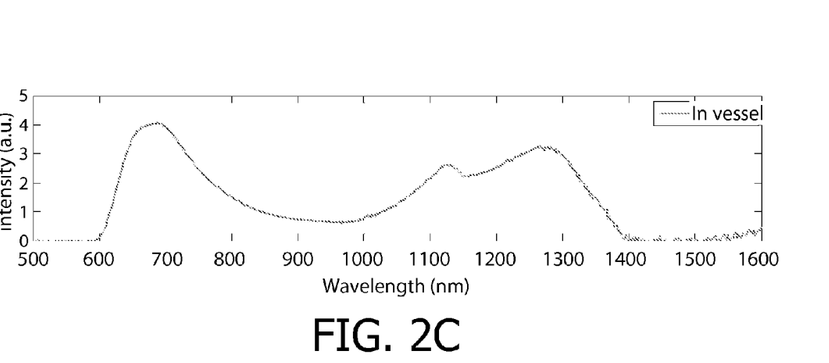

In a further specific embodiment of the system 101, the measurement arrangement 120 is alternatively configured for measuring spectral contents of the electromagnetic spectrum of the incoming beam 116. FIG. 2A depicts the reflectance spectrum for tissue, FIG. 2B displays the reflectance spectrum for a wall of a blood vessel and FIG. 2C shows the reflectance spectrum of blood. The intensity of the reflectance spectra is expressed in a dimensionless manner. The reference electromagnetic spectrum may either be the reflectance spectrum of tissue as depicted in FIG. 2A or the reflectance spectrum of blood as depicted in FIG. 2C. According to FIG. 2A and FIG. 2C the reflectance spectra of blood and tissue significantly differ, particularly for wavelengths below 570 nm and for wavelengths between 650 and 750 nm. These differences are attributable to the relatively strong absorption of green light i.e. electromagnetic radiation having wavelengths in the range of 520 to 570 nm by blood on the one hand, and the relatively strong reflection of red light i.e. electromagnetic radiation having wavelengths in the range of 630 to 740 nm by blood on the other hand. Therefore, in a further embodiment of the system according to the invention, the measurement arrangement is arranged for measuring the spectral contents of the electromagnetic spectrum of the incoming beam 116 at a particular wavelength, preferably a wavelength in the range of 630 to 730 nm, e.g. 700 nm. The latter range of wavelengths enables robustly and accurately distinguishing between blood and the wall of the blood vessel, see FIGS. 2B and 2C. Furthermore, by considering a wavelength between 630 and 730 nm, a signal of larger amplitude is obtained thereby increasing the signal-to-noise ratio associated with the parameter 122 and consequently improving the measurement accuracy of the system 101. In a further embodiment of the system according to the invention, the measurement arrangement is arranged for measuring the spectral contents of the electromagnetic spectrum of the incoming beam 116 at a plurality of particular wavelengths, preferably a plurality of wavelengths in the range of 630 to 730 nm, e.g. 650 nm, 680 nm and 710 nm.

Figure 3A:
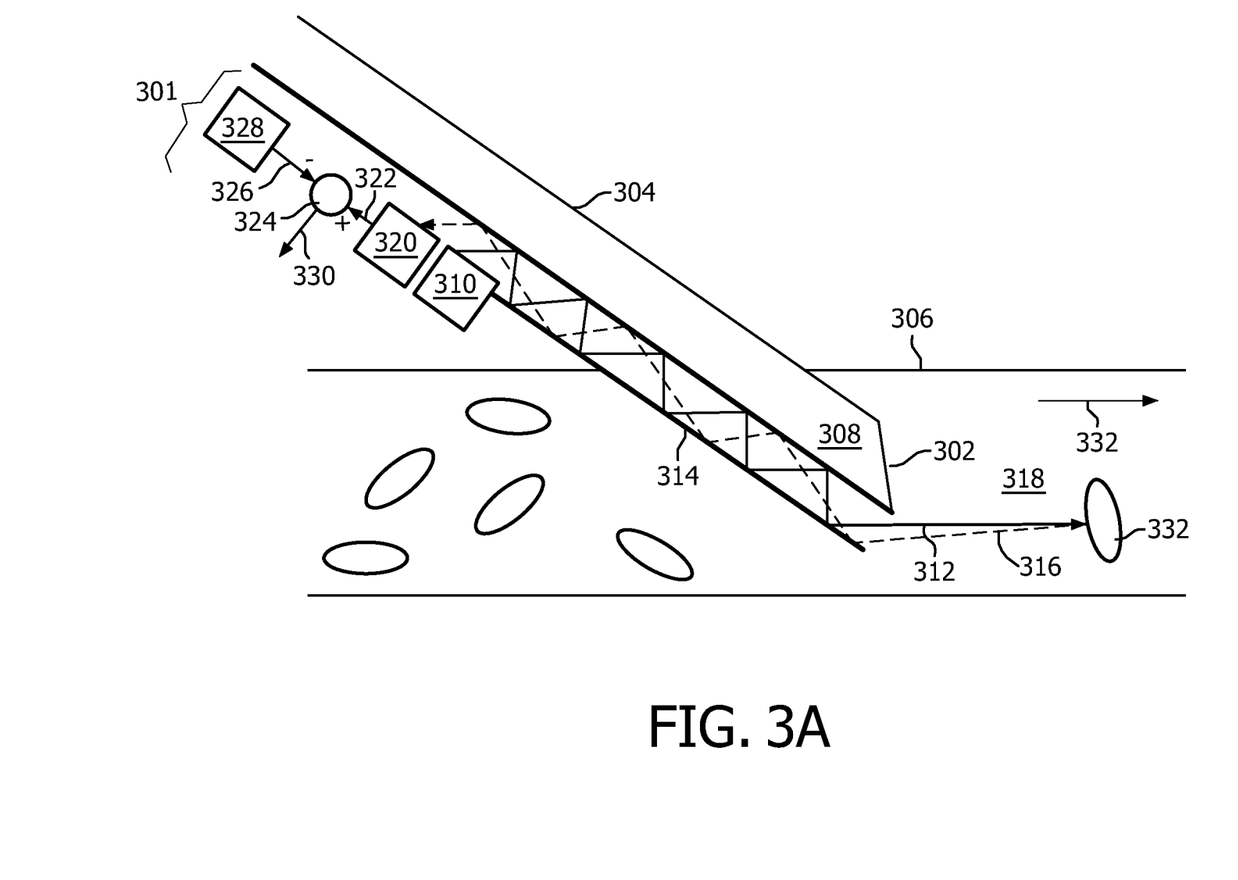
FIG. 3 schematically depicts embodiments of the system according to the invention wherein the guideway is integrated with the tube.

FIG. 3A schematically displays a system 301 for monitoring a position of a distal end 302 of a tube 304 with respect to a blood vessel 306. In this particular embodiment, the tube 304 is employed for intravenous supply of a liquid 308, nonetheless, it may equally well perform for the purpose of taking samples from the blood vessel 306. The system 301 comprises a source 310 for generating an outgoing beam 312 of electromagnetic radiation having a predefined electromagnetic spectrum. The system 301 furthermore comprises a guideway 314 for transferring the outgoing beam 312 towards the distal end 302 of the tube 304. In this particular embodiment, a wall 313 of the tube 304 is arranged to perform as the guide way 314. As a result the tube 304 and the guideway 314 are effectively integrated into a single component. The wall 313 employs the principle of total internal reflection. The guideway 314 is furthermore configured for transferring an incoming beam 316 of electromagnetic radiation reflected by surroundings 318 of the distal end 302 in response to said outgoing beam 312 of electromagnetic radiation to a measurement arrangement 320. The measurement arrangement 320 is arranged for measuring a parameter 322 associated with an electromagnetic spectrum of the incoming beam 316 of electromagnetic radiation. The parameter 322 may be time dependency of or spectral contents of the electromagnetic spectrum of the incoming beam 316. The system 301 furthermore comprises a comparator arrangement 324 configured for comparing the parameter 322 with a reference parameter 326 associated with a reference electromagnetic spectrum. The reference electromagnetic spectrum is attainable by the incoming beam 316 in response to the outgoing beam 312 if the distal end 302 were positioned at some predefined location inside the mammal patient. Herein, the predefined location may either be the blood vessel 306 or the tissue surrounding said blood vessel 306. In this specific example, a memory 328 is arranged for storing the reference parameter 326. An output 330 of the comparator arrangement 324 allows the medical professional involved to take appropriate measures if the system 301 monitors that the position of the distal end 302 is not in the blood vessel 306.

Figure 3B:
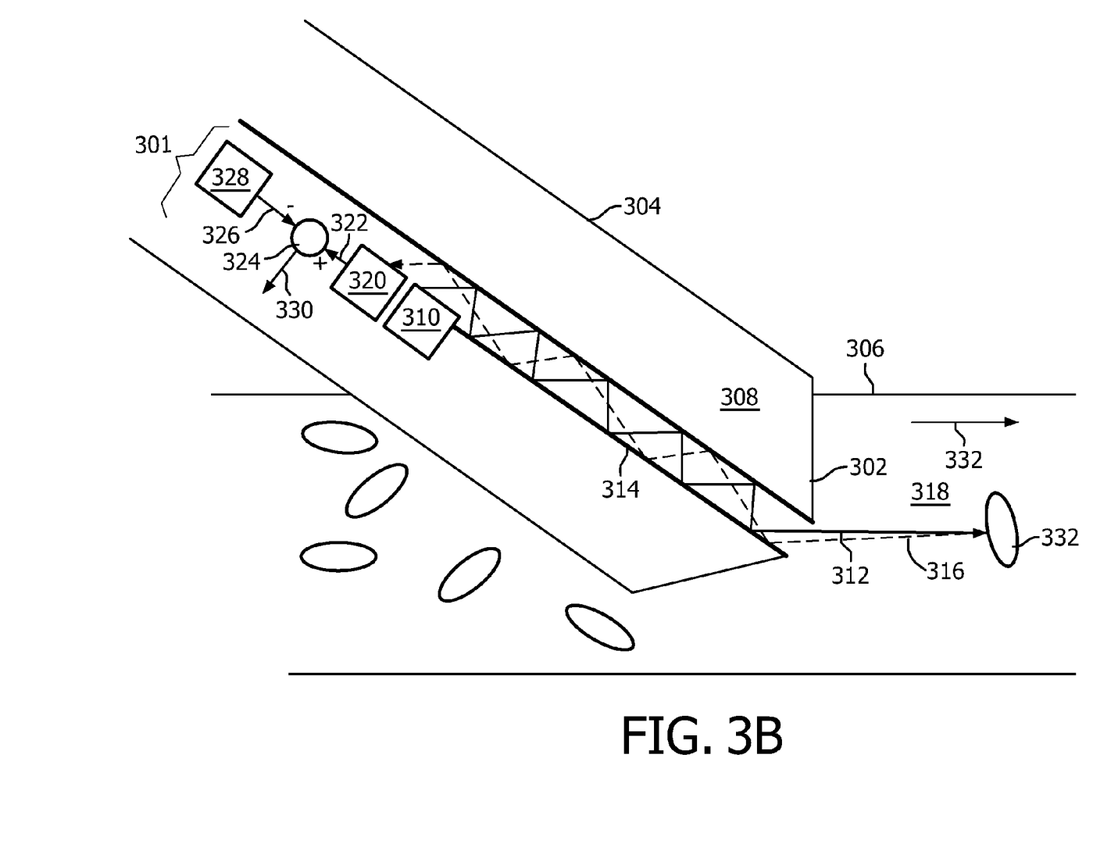

In FIG. 3B, identical reference numbers identify identical elements. In the specific embodiment displayed in FIG. 3B, the guideway 314 comprises an optical fiber. Therefore, in the particular embodiment displayed in FIG. 3B, the tube 304 and the guideway 314 are integrated into a single component. The optical fiber makes use of total internal reflection.

Figure 4:
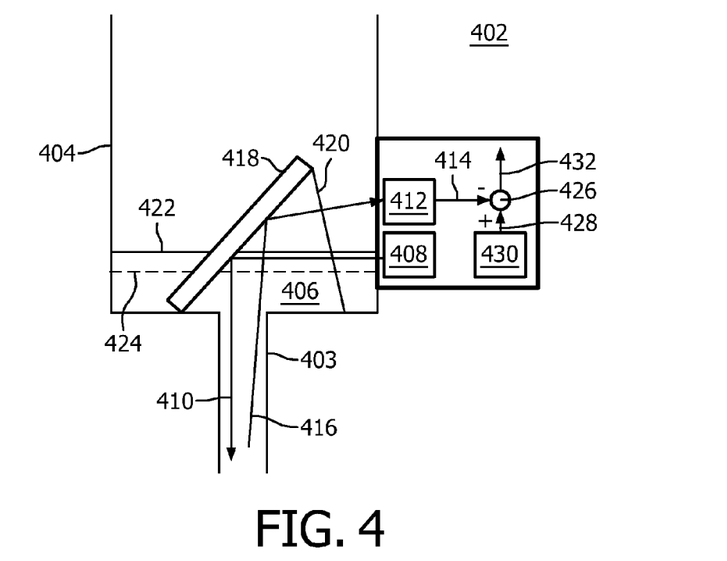
FIG. 4 schematically shows an embodiment of the system according to the invention comprising a drip chamber.

FIG. 4 schematically displays a system 402 for monitoring the position of a distal end (not depicted) of a tube 403 relative to a blood vessel (not depicted). The system 402 is releasably mounted to a drip chamber 404. The drip chamber 404 is configured for storing a liquid 406 which is to be intravenously supplied to a mammal patient (not shown). The system 402 comprises a source 408 for generating an outgoing beam 410 having a predefined electromagnetic spectrum. The system 402 furthermore comprises a measurement arrangement 412 for measuring a parameter 414 associated with an incoming beam 416 reflected by surroundings of the tube's distal end. The system 402 comprises a guideway for transferring the outgoing beam 410 towards the distal end of the tube 403 and for guiding the incoming beam 416 to the measurement arrangement 412, which guideway is embodied by the liquid 406 itself. Alternatively, for instance an optical fiber may be equally well employed for the purpose of defining a guideway. The system 402 furthermore comprises a mirror 418 and an optical element 420. The optical element comprises a transparent part in response to coverage by the liquid 406 and a reflective part in response to non-coverage by the liquid 406 i.e. in response to coverage by air. Hence, optical element 420 will pass on the outgoing beam 410 merely if said outgoing beam interacts with the part submerged in the fluid 406. As a result, if the liquid is at any level above critical level 422, outgoing beam 410 will pass optical element 420 whereas the outgoing beam is reflected by the optical element 420 if the liquid is for instance at level 424, which reflectance provides for an indication that the amount of liquid 406 in the drip chamber 404 is below the critical value. The system 402 furthermore comprises a comparator arrangement 426 for comparing the parameter 414 with a reference parameter 428 which may be stored in a memory 430. The comparator arrangement 426 generates information 432 indicative of the position of the tube's distal end relative to the blood vessel of the mammal.

Figure 5:
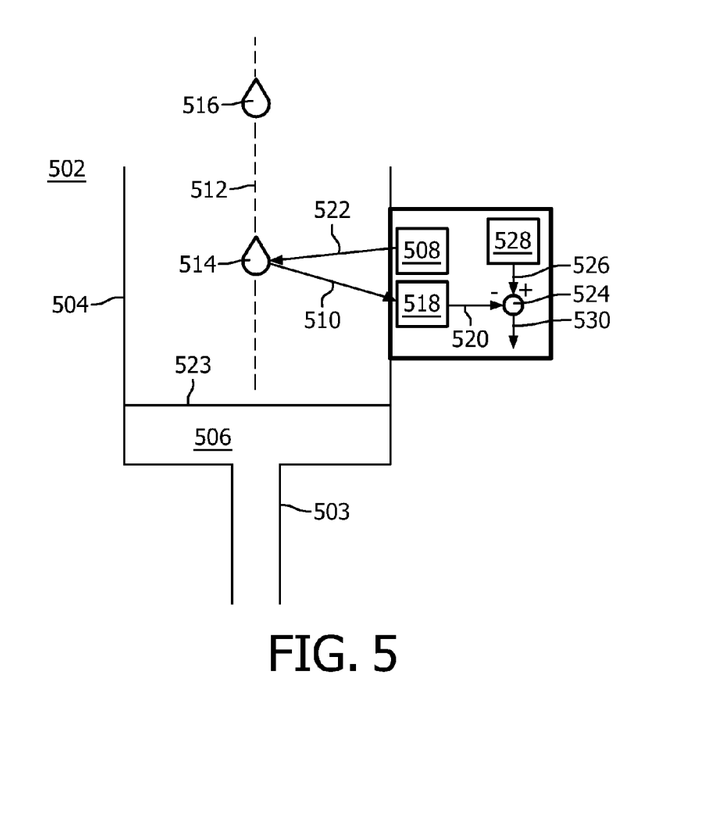
FIG. 5 schematically depicts an embodiment of the system according to the invention wherein the outgoing beam is provided with an orientation intersecting the liquid dropping from a liquid container.

FIG. 5 schematically displays a system 502 for monitoring the position of a distal end (not depicted) of a tube 503 relative to a blood vessel (not depicted). The system 502 is releasably mounted to a drip chamber 504. The drip chamber 504 is configured for storing a liquid 506 which is to be intravenously supplied to a mammal (not shown). The system 502 comprises a source 508 for generating an outgoing beam 510 having a predefined electromagnetic spectrum. The source 508 is configured for providing the outgoing beam 510 with an orientation intersecting an imaginary axis 512 along which the liquid drops via droplets 514 and 516 from a liquid container (not shown) towards the tube 503 during operational conditions. The system 502 furthermore comprises a measurement arrangement 518 for measuring a parameter 520 associated with an incoming beam 522. The incoming beam 522 is reflected either by droplets 514 and 516, or in the absence of such droplets, by the surroundings of the tube's distal end thereby enabling monitoring the position of the tube's distal end with respect to the blood vessel. The time span between reflectance of the outgoing beam 510 by droplets 514 and 516 provides a measure for the liquid drop rate from the liquid container to the drip chamber 504. Presuming the liquid level 523 has attained a stationary value, the liquid drop rate constitutes an accurate measure for the rate at which the liquid 506 is intravenously supplied towards a mammal patient (not shown). The system 502 comprises a guideway for transferring the outgoing beam 510 towards the distal end of the tube 503 and for guiding the incoming beam 522 to the measurement arrangement 518, which guideway is embodied by the liquid 506 itself. The system 502 furthermore comprises a comparator arrangement 524 for comparing the parameter 520 with a reference parameter 526 which may be stored in a memory 528. The information 530 generated by the comparator arrangement 524 during operational conditions, is indicative of the position of the tube's distal end relative to the blood vessel of the mammal patient. It is to be noted that the source 508 and the measurement arrangement 518 may alternatively be positioned on opposite sides of the drip chamber 504.

Figure 6:
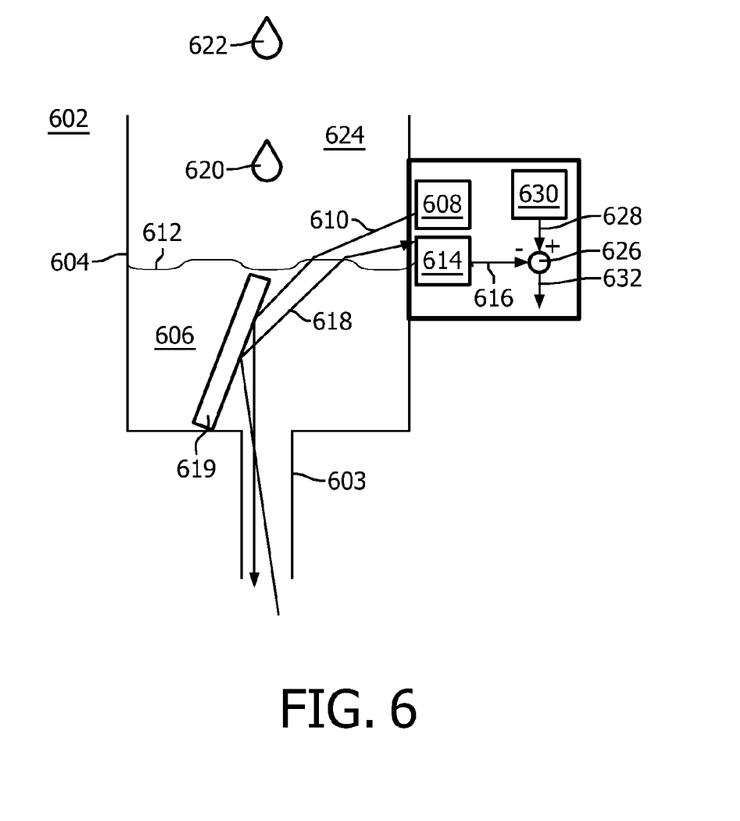
FIG. 6 schematically shows an embodiment of the system according to the invention wherein the outgoing beam is provided with an orientation intersecting an interface of the liquid in the drip chamber.

FIG. 6 schematically depicts a system 602 for monitoring the position of a distal end (not depicted) of a tube 603 with respect to a blood vessel (not depicted) of a mammal (not shown). The system 602 is releasably mounted to a drip chamber 604. The drip chamber 604 is configured for storing a liquid 606 to be intravenously supplied to the mammal patient. The system 602 comprises a source 608 for generating an outgoing beam 610 having a predefined electromagnetic spectrum. The source 608 is configured for providing the outgoing beam 610 with an orientation intersecting an interface 612 of the liquid 606 in the drip chamber 604. The system 602 furthermore comprises a measurement arrangement 614 for measuring a parameter 616 associated with an incoming beam 618. The system 602 comprises an optical element 619 e.g. a mirror to redirect the outgoing beam 610 towards the guideway, which guideway is arranged for transferring the outgoing beam 610 towards the distal end of the tube 603 and for guiding the incoming beam 618 to the measurement arrangement 614. During operation, liquid drops 620 and 622 falling from a liquid container (not shown) under the influence of gravity to the drip chamber 604 cause surface waves at interface 612. In response to said surface waves, the orientation along which the outgoing beam 610 is refracted by the interface 612, modifies direction. Furthermore, the angle between the incoming beam 618 and the interface 612 may become such large that it exceeds the critical angle of the interface 612 between air 624 and the liquid 606. Consequently, total inner reflection rather than refraction is obtained at the interface 612. Therefore the frequency at which reflection and refraction by the interface 612 of the incoming beam 618 alternate, provides a measure for the liquid drop rate from the liquid container to the drip chamber 604. Presuming the amount of liquid 606 in the drip chamber 604 has attained a stationary value, the liquid drop rate constitutes an accurate measure for the rate at which the liquid 606 is being intravenously supplied towards the mammal patient. The system 602 furthermore comprises a comparator arrangement 626 configured for comparing the parameter 616 with a reference parameter 628 stored in a memory 630, and for accordingly generating information 632 indicative of the position of the tube's distal end relative to the blood vessel of the mammal patient. Alternatively the measurement arrangement 614 may comprise a position sensitive detector known per se.

While the invention has been illustrated and described in detail in the drawings and in the foregoing description, the illustrations and the description are to be considered illustrative or exemplary and not restrictive. The invention is not limited to the disclosed embodiments. It is noted that the system according to the invention and all its components can be made by applying processes and materials known per se. In the set of claims and the description the word "comprising" does not exclude other elements and the indefinite article "a" or "an" does not exclude a plurality. Any reference signs in the claims should not be construed as limiting the scope. It is further noted that all possible combinations of features as defined in the set of claims are part of the invention.

The invention claimed is:

1. A system for monitoring a position of a distal end of a tube with respect to a blood vessel of a mammal comprising:
   a source for generating an outgoing beam of electromagnetic radiation having a predefined electromagnetic spectrum,
   a guideway comprising a single optical fiber for guiding the outgoing beam to the distal end, and for guiding an incoming beam of electromagnetic radiation reflected by surroundings of the distal end in response to said outgoing beam to a measurement arrangement, the measurement arrangement configured to measure a parameter associated with an electromagnetic spectrum of the incoming beam, and
   a comparator arrangement configured to compare said parameter with a reference parameter associated with a reference electromagnetic spectrum representing a predefined location of the distal end inside the mammal; and
   a drip chamber for temporarily storing a liquid dripping from a liquid container during use, wherein the drip chamber comprises an optical element configured for assisting the guideway in guiding the outgoing beam of electromagnetic radiation from the source to the distal end, which optical element has a transparent part in response to coverage by the liquid in the drip chamber and a reflective part in response to non-coverage by the liquid in the drip chamber; or wherein the source is configured for providing the outgoing beam of electromagnetic radiation with an orientation intersecting an imaginary axis along which the liquid drops from the liquid container towards the tube during operational conditions; or wherein the source is configured for providing the outgoing beam of electromagnetic radiation with an orientation intersecting an interface of the liquid in the drip chamber.

2. The system according to claim 1, wherein the reference electromagnetic spectrum represents the situation in which the predefined location is inside the blood vessel.

3. The system according to claim 2, wherein the parameter is time dependency.

4. The system according to claim 1, wherein the parameter is spectral contents.

5. The system according to claim 4, wherein the parameter is spectral contents at a specific wavelength.

6. The system according to claim 5, wherein the specific wavelength is in the range of 630 nm to 730 nm.

7. The system according to claim 1, wherein a wall of the tube is configured for performing as the guideway.

8. The system according to claim 1, wherein the guideway is arranged for receiving a liquid, and the single optical fiber guides the outgoing beam and the incoming beam.

9. A system for monitoring a position of a distal end of a tube with respect to a blood vessel of a mammal comprising:
   a source configured to generate an outgoing beam of electromagnetic radiation having a predefined electromagnetic spectrum,
   a guideway configured to guide the outgoing beam to the distal end, and for guiding an incoming beam of electromagnetic radiation reflected by surroundings of the distal end in response to said outgoing beam to a measurement arrangement, the measurement arrangement configured to measure a parameter associated with an electromagnetic spectrum of the incoming beam,
   a comparator arrangement configured to compare said parameter with a reference parameter associated with a reference electromagnetic spectrum representing a predefined location of the distal end inside the mammal, and
   a drip chamber configured to store temporally a liquid dripping from a liquid container during use, wherein the drip chamber comprises an optical element configured for assisting the guideway in guiding the outgoing beam of electromagnetic radiation from the source to the distal end, which optical element has a transparent part in response to coverage by the liquid in the drip chamber and a reflective part in response to non-coverage by the liquid in the drip chamber.

10. The system according to claim 9, wherein the reference electromagnetic spectrum represents the situation in which the predefined location is inside the blood vessel.

11. The system according to claim 10, wherein the parameter is time dependency.

12. The system according to claim 9, wherein the parameter is spectral contents.

13. The system according to claim 12, wherein the parameter is spectral contents at a specific wavelength.

14. The system according to claim 13, wherein the specific wavelength is in the range of 630 nm to 730 nm.

15. The system according to claim 9, wherein a wall of the tube is the guideway.

16. The system according to claim 9, wherein the guideway is arranged for receiving a liquid to guide the outgoing beam and the incoming beam.

17. The system according to claim 9, wherein the tube comprises an optical fiber as the guideway.

18. A system for monitoring a position of a distal end of a tube with respect to a blood vessel of a mammal comprising:
- a source configured to generate an outgoing beam of electromagnetic radiation having a predefined electromagnetic spectrum,
- a guideway configured to guide the outgoing beam to the distal end, and for guiding an incoming beam of electromagnetic radiation reflected by surroundings of the distal end in response to said outgoing beam to a measurement arrangement, the measurement arrangement configured to measure a parameter associated with an electromagnetic spectrum of the incoming beam, and
- a comparator arrangement configured to compare said parameter with a reference parameter associated with a reference electromagnetic spectrum representing a predefined location of the distal end inside the mammal,
- a drip chamber configured to store temporally a liquid dripping from a liquid container during use, wherein the source is configured for providing the outgoing beam of electromagnetic radiation with an orientation intersecting an imaginary axis along which the liquid drops from the liquid container towards the tube during operational conditions.

19. The system according to claim 18, wherein the reference electromagnetic spectrum represents the situation in which the predefined location is inside the blood vessel.

20. The system according to claim 19, wherein the parameter is time dependency.

21. The system according to claim 18, wherein the parameter is spectral contents.

22. The system according to claim 21, wherein the parameter is spectral contents at a specific wavelength.

23. The system according to claim 22, wherein the specific wavelength is in the range of 630 nm to 730 nm.

24. The system according to claim 18, wherein a wall of the tube is the guideway.

25. The system according to claim 18, wherein the guideway is arranged for receiving a liquid to guide the outgoing beam and the incoming beam.

26. The system according to claim 18, the tube comprises an optical fiber as the guideway.

27. A system for monitoring a position of a distal end of a tube with respect to a blood vessel of a mammal comprising:
- a source configured to generate an outgoing beam of electromagnetic radiation having a predefined electromagnetic spectrum,
- a guideway configured to guide the outgoing beam to the distal end, and for guiding an incoming beam of electromagnetic radiation reflected by surroundings of the distal end in response to said outgoing beam to a measurement arrangement, the measurement arrangement configured to measure a parameter associated with an electromagnetic spectrum of the incoming beam, and
- a comparator arrangement configured to compare said parameter with a reference parameter associated with a reference electromagnetic spectrum representing a predefined location of the distal end inside the mammal, and
- a drip chamber configured to store temporally a liquid dripping from a liquid container during use, wherein the source is configured for providing the outgoing beam of electromagnetic radiation with an orientation intersecting an interface of the liquid in the drip chamber.

28. The system according to claim 27, wherein the reference electromagnetic spectrum represents the situation in which the predefined location is inside the blood vessel.

29. The system according to claim 28, wherein the parameter is time dependency.

30. The system according to claim 27, wherein the parameter is spectral contents.

31. The system according to claim 30, wherein the parameter is spectral contents at a specific wavelength.

32. The system according to claim 31, wherein the specific wavelength is in the range of 630 nm to 730 nm.

33. The system according to claim 27, wherein a wall of the tube is configured for performing as the guideway.

34. The system according to claim 27, wherein the guideway is arranged for receiving a liquid to guide the outgoing beam and the incoming beam.

35. The system according to claim 27, wherein the tube comprises an optical fiber for performing as the guideway.

* * * * *